United States Patent
Sun et al.

(10) Patent No.: US 11,345,761 B2
(45) Date of Patent: May 31, 2022

(54) ESTERIFIED SELENIUM POLYSACCHARIDE AND PREPARATION METHOD AND USE THEREFOR

(71) Applicant: AI-MAY ZHONG KE SELENIUM TECHNOLOGY (TIANJIN) CO., LTD, Tianjin (CN)

(72) Inventors: Yumin Sun, Tianjin (CN); Haiquan Liu, Tianjin (CN)

(73) Assignee: AI-MAY ZHONG KE SELENIUM TECHNOLOGY (TIANJIN) CO., LTD, Tianjin (CN)

(*) Notice: Subject to any disclaimer, the term of this patent is extended or adjusted under 35 U.S.C. 154(b) by 0 days.

(21) Appl. No.: 17/256,015

(22) PCT Filed: Oct. 16, 2018

(86) PCT No.: PCT/CN2018/110494
§ 371 (c)(1),
(2) Date: Dec. 24, 2020

(87) PCT Pub. No.: WO2020/000788
PCT Pub. Date: Jan. 2, 2020

(65) Prior Publication Data
US 2021/0221922 A1 Jul. 22, 2021

(30) Foreign Application Priority Data
Jun. 26, 2018 (CN) .......................... 201810672663.6

(51) Int. Cl.
*C08B 37/00* (2006.01)

(52) U.S. Cl.
CPC ................................ *C08B 37/0003* (2013.01)

(58) Field of Classification Search
None
See application file for complete search history.

(56) References Cited

FOREIGN PATENT DOCUMENTS

| CN | 1560088 A | 1/2005 |
|----|-----------|--------|
| CN | 101190951 A | 6/2008 |
| CN | 101560267 A | 10/2009 |
| CN | 101654486 A | 2/2010 |
| CN | 105199007 A | 12/2015 |
| CN | 107629134 A | 1/2018 |

*Primary Examiner* — Layla D Berry
(74) *Attorney, Agent, or Firm* — Bayramoglu Law Offices L.L.C

(57) ABSTRACT

A preparation method for an esterified selenium polysaccharide includes the steps of: adding O=SeCl$_2$ dropwise to a triethylamine-containing D-galactose allyl glucoside solution and reacting at room temperature to obtain 3,4-oxo-cyclo selenite galactose allyl glucoside; mixing NaHCO$_3$ into a polysaccharide solution, adding acryloyl chloride dropwise to the polysaccharide solution and maintaining a temperature of a reaction solution to not exceed 40° C. during a dropwise addition to obtain acrylated polysaccharide; and performing a displacement reaction of the acrylated polysaccharide with the 3,4-oxo-cyclo selenite galactose allyl glucoside under an action of a Ru catalyst to obtain the esterified selenium polysaccharide. The esterified selenium polysaccharide prepared by the preparation method improves an immunity of a tested organism by increasing a selenium content in blood.

16 Claims, 1 Drawing Sheet

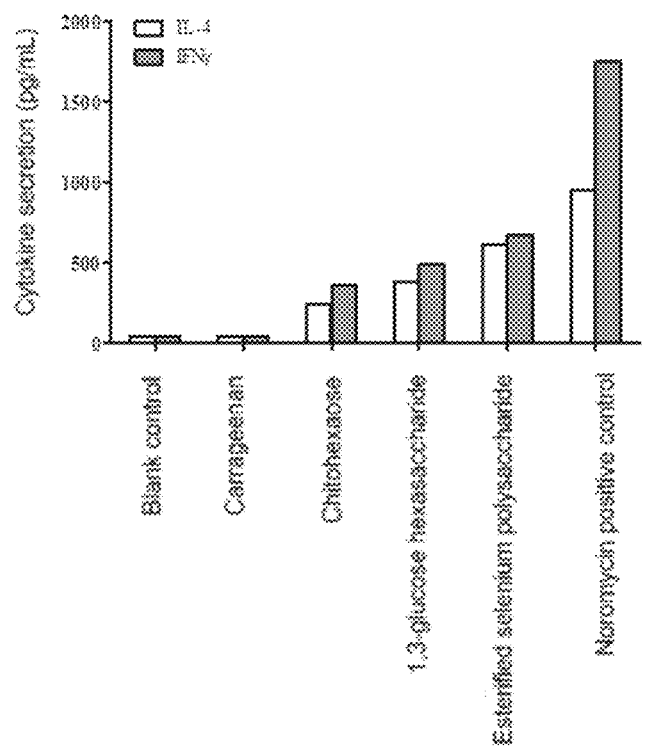

ESTERIFIED SELENIUM POLYSACCHARIDE AND PREPARATION METHOD AND USE THEREFOR

CROSS REFERENCE TO RELATED APPLICATIONS

This application is the national stage entry of International Application No. PCT/CN2018/110494, filed on Oct. 16, 2018, which is based upon and claims priority to Chinese Patent Application No. 201810672663.6, filed on Jun. 26, 2018, the entire contents of which are incorporated herein by reference.

TECHNICAL FIELD

The invention relates to the technical field of selenium polysaccharides, in particular to an esterified selenium polysaccharide, and preparation method and use therefor.

BACKGROUND

Selenium (Se) is an indispensable trace element for the human body, which plays an important role in improving the immune function of life, anti-cancer, anti-oxidation, and preventing nutritional liver necrosis, and the like. In biological metabolism, selenium is also an active component of glutathione peroxidase, therefore, it is extremely important to the human body. However, selenium is unevenly distributed on the earth, and about three-fifths of China is short of selenium. The content of selenium in ordinary food is extremely low, and the effect of selenium supplementation is generally not achieved. In nature, selenium mainly exists in two forms: inorganic selenium and organic selenium. Compared with inorganic selenium, organic selenium is a safer and more active selenium-containing substance, and it is more significant than inorganic selenium in stimulating immune response. The main sources of organic selenium are natural selenium-rich organisms and artificial synthesis. Among many organic selenium-rich substances, selenium polysaccharides have received great attention. As an organic selenium compound, the selenium polysaccharide has the activity of that of both selenium and polysaccharide, and the selenized polysaccharide is easier to be absorbed and utilized by organisms. In recent years, many selenium-rich foods and products have appeared, in which selenium polysaccharides are the main components. The preparation method of selenium polysaccharides includes origination from natural selenium-containing plant polysaccharides, metabolism of selenium polysaccharides by microbial enrichment culture and artificial synthesis of selenium polysaccharides. Crops grown in selenium-rich soil are rich in selenium, and the resultant product is safe but the selenium content is very low, making it basically impossible to achieve the normal metabolic balance of the selenium content necessary for the blood. Artificial synthesis of selenium polysaccharides is a relatively convenient and controllable method.

At present, in domestic and foreign documents and patents, selenium polysaccharides were mainly prepared by adopting the following three methods: selenization modification of polysaccharides using monomeric selenium, seleninic acid or sodium selenite under mild conditions; modification by using chemically active intermediates with acyl chloride structure as a selenization reagent; graft of selenium-containing functional genes to polysaccharide molecules. Liang Shuxuan et al. performed the reaction of sodium selenate with $Lycium\ barbarum$ polysaccharides using glacial acetic acid for catalyzation; Li Zhizhou et al. prepared polyporus selenium polysaccharides using polyporus polysaccharide and sodium selenite as raw materials by using chemical synthesis method, in which continuous or ultrasonic-assisted chemical synthesis processes were used. The disadvantages are the site for selenization is not clear, the degree of selenization is uncertain, and the relatively large amount of toxic inorganic selenium components mixed in polysaccharides of high molecular weight cannot be completely removed. Patent CN 1560088A disclosed a method for preparing selenized glucomannan. The elemental selenium was oxidized to $Se^{6+}$ under the action of an oxidizing agent. Ethanol and hydrochloric acid were added to an aqueous solution of $Se^{6+}$ ions to obtain a selenized reaction solution. Then the selenized reaction solution was reacted with glucomannan to produce selenized glucomannan. The obtained selenized glucomannan has relatively low selenium content, and the selenium in the derivative is $Se^{6+}$. Patent ZL 88103347 disclosed a method for preparing a selenized carrageenan, which was performed by using selenium powder as a raw material, dissolving it with nitric acid to prepare a selenium solution, and adding Kappa-carrageenan solution for selenization reaction. However, the product obtained by this method has low selenium content (2500-15000 ppm) as well as a toxic by-product hydrogen selenide. Patent ZL 200910162003.4 disclosed a method for preparing selenized Artemisiaareraria polysaccharide or $Potentilla\ anserina$ polysaccharide by using organic method, which was performed by reacting $Potentilla\ anserina$ polysaccharide or Artemisiaareraria polysaccharide with selenyl chloride to obtain selenized Artemisiaareraria polysaccharide or $Potentilla\ anserina$ polysaccharide. However, the selenite chloride used in this method is difficult to synthesize as well as toxic. During the reaction process, when the selenite chloride is added, it will be oxidized when exposed to the air, and the obtained selenite chloride may contain impurities such as selenoyl chloride.

The polysaccharide selenization modification technology mentioned in the above patents and documents generally has the disadvantages of complex preparation and high toxicity of selenium-containing intermediates, long reaction time, low selenium content and yield of selenized polysaccharides, many side reactions, and unknown biological effects and the like.

SUMMARY

In order to overcome the shortcomings of the prior art, the present invention provides an esterified selenium polysaccharide and preparation method and use therefor. The obtained esterified selenium polysaccharide has clear selenium binding sites and high selenium content with no toxic side effects.

The technical solutions of the present invention are as follows:

The present invention provides a method for preparing an esterified selenium polysaccharide, comprising the following steps:

(1) adding 1~5 equivalents of O=SeCl$_2$ dropwise to a D-galactose allyl glucoside solution containing 1~5 equivalents of triethylamine at 0° C. under protection of nitrogen, reacting at room temperature for 1~4 hours then pouring into a water phase, and extracting with ethyl acetate to obtain 3,4-oxo-cyclo selenite galactose allyl glucoside;

(2) suspending a polysaccharide in a solvent, mixing with NaHCO$_3$, adding acryloyl chloride dropwise to the polysaccharide solution, and maintaining the temperature of the reaction solution to not exceed 40° C. during the dropwise addition, after completion of the reaction, dissolving the reaction solution in water and performing alcohol precipitation to obtain acrylated polysaccharide; and (3) dissolving the acrylated polysaccharide in a solvent, performing a displacement reaction of the acrylated polysaccharide with the 3,4-oxo-cyclo selenite galactose allyl glucoside under the action of a Ru catalyst, dispersing the obtained reaction solution in a water phase and performing alcohol precipitation to obtain an esterified selenium polysaccharide.

Preferably, in step (2), the molar ratio of the polysaccharide to acryloyl chloride is 1:1~50.

Preferably, in step (2), the molar ratio of the polysaccharide to sodium bicarbonate is 1:5~50.

Further preferably, in step (2), the reaction is completed 2~3 hours after the dropwise addition is stopped.

Preferably, in step (3), the molar ratio of the acrylated polysaccharide to the 3,4-oxo-cyclo selenite galactose allyl glucoside is 1:1~4.

Further preferably, in step (3), the displacement reaction is completed within 4~5 hours.

Preferably, step (1) further comprises a purification step after extracting with ethyl acetate: washing the extract with saturated brine, drying the organic phase and evaporating it to dryness, and loading it on chromatography column to obtain 3,4-oxo-cyclo selenite galactose allyl glucoside.

Preferably, the polysaccharide is a water-soluble natural polysaccharide containing a primary hydroxyl group at the 6-position.

The present invention also includes the esterified selenium polysaccharide prepared by any one of the methods described above, having a structural formula of.

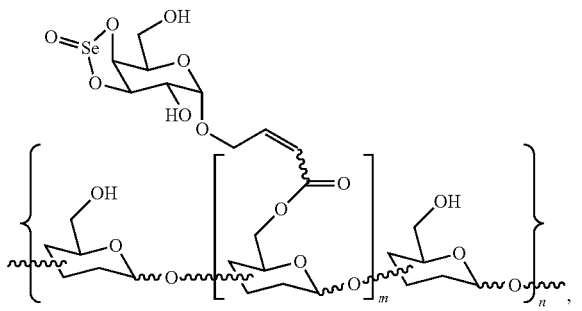

wherein M is the number of sugar units selenized, and N is the number of sugar units of natural polysaccharides.

Preferably, the organic selenium content of the esterified selenium polysaccharide reaches 10,000 to 100,000 ppm.

The present invention also includes the use of the esterified selenium polysaccharide described above for improving immunity for non-therapeutic purposes.

Compared with the prior art, the present invention has the following advantages:

The present invention prepares an esterified selenium product with controllable selenium content through the displacement reaction of 3,4-oxo-cyclo selenite galactose allyl glucoside and acrylated polysaccharide. The selenium-containing intermediate 3,4-oxo-cyclo selenite galactose allyl glucoside is simple to prepare, and the yield of which is greater than 90%; the selenium-containing intermediate can be either purified or used directly without purification during the preparation process, and the obtained selenium-containing intermediates are non-toxic. In the synthesis process of the esterified selenium polysaccharide, the replacement reaction are simple in conditions with short reaction time and high yield. The selenium content of the obtained esterified selenium polysaccharide can reach 10,000 to 100,000 ppm, which is adjustable.

In the esterified selenium polysaccharide molecule prepared by the invention, selenium element exists in the form of organic ester, and the selenium atom combines with two sugar hydroxyl groups at the same time to form a selenite unit with a cyclic structure. The organic compound carrier forming the esterified selenium structure is a polysaccharide substance, which has the potential to increase the selenium content in blood to improve many immune function, and can significantly improve the immunity of the test organism by increasing the selenium content in blood.

BRIEF DESCRIPTION OF THE DRAWINGS

In order to explain the embodiments of the present invention or the technical solutions in the prior art more clearly, the drawings that need to be used in the description of the embodiments or the prior art will be briefly introduced in the following. Obviously, the drawings in the following description are merely some of the embodiments of the present invention, and for those of ordinary skill in the art other drawings can be obtained based on these drawings without creative work.

FIGURE shows the maximum expression levels of cytokines IL-4 and IFN-γ in Example 4.

DETAILED DESCRIPTION OF THE EMBODIMENTS

The technical solutions in the embodiments of the present invention are described clearly and completely in the following. Obviously, the described embodiments are merely a part of the embodiments of the present invention, rather than all the embodiments. Based on the embodiments of the present invention, all other embodiments obtained by those of ordinary skill in the art without creative work shall fall within the protection scope of the present invention.

The present invention provides a method for preparing an esterified selenium polysaccharide, comprising the following steps:

(1) adding 1~5 equivalents of O=SeCl$_2$ dropwise to a D-galactose allyl glucoside solution containing 1~5 equivalents of triethylamine at 0° C. under protection of nitrogen, reacting at room temperature for 1~4 hours then pouring into a water phase, and extracting with ethyl acetate to obtain 3,4-oxo-cyclo selenite galactose allyl glucoside;

(2) suspending a polysaccharide in a solvent, mixing with NaHCO$_3$, adding acryloyl chloride dropwise to the polysaccharide solution, and maintaining the temperature of the reaction solution to not exceed 40° C. during the dropwise addition, after completion of the reaction, dissolving the reaction solution in water and performing alcohol precipitation to obtain acrylated polysaccharide; and (3) dissolving the acrylated polysaccharide in a solvent, performing a displacement reaction of the acrylated polysaccharide with the 3,4-oxo-cyclo selenite galactose allyl glucoside under the action of a Ru catalyst, dispersing the obtained reaction solution in a water phase and performing alcohol precipitation to obtain an esterified selenium polysaccharide;

wherein step (1) and step (2) are not limited in order.

The reaction processes of the esterified selenium polysaccharide of the present invention are as follows:

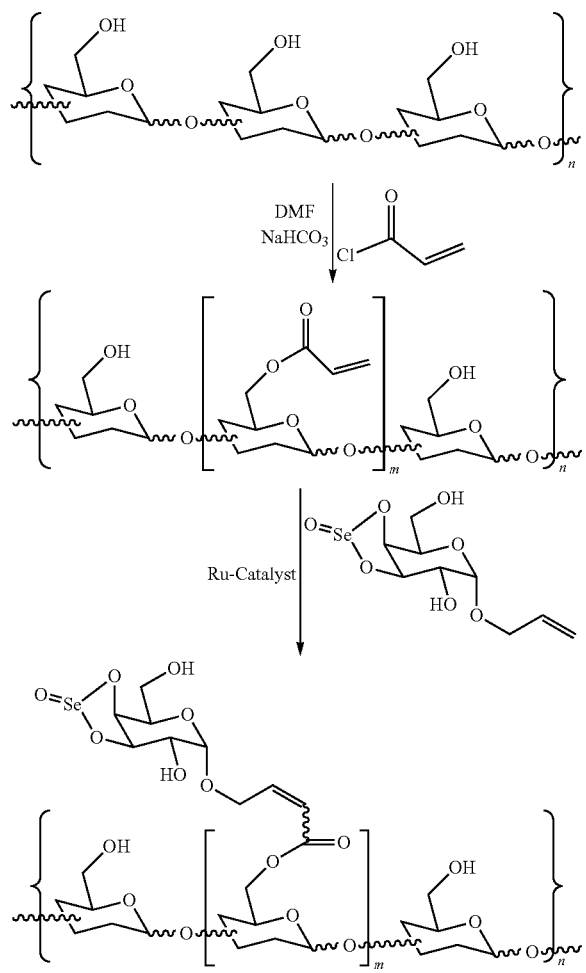

In the step of synthesizing 3,4-oxo-cyclo selenite galactose allyl glucoside in the present invention, O=SeCl₂ is added dropwise to a triethylamine-containing D-galactose allyl glucoside solution under the protection of nitrogen at 0° C., and the displacement reaction occurs at room temperature. In the step, D-galactose allyl glycoside is preferably dissolved in DMF or DMSO to form a D-galactose allyl glycoside solution. In the present invention, the amount of O=SeCl₂ is preferably 2~4 equivalents, and triethylamine is preferably added in the amount of 2~4 equivalents. In the present invention, the above-mentioned reaction is lasted for preferably 2~3 hours. After the completion of the reaction, the reaction solution was poured into the water phase and extracted with ethyl acetate to obtain 3,4-oxo-cyclo selenite galactose allyl glucoside. Preferably, in the present invention a purification step after the ethyl acetate extraction is further included washing the extract with saturated brine, drying the organic phase and evaporating it to dryness, and loading it on chromatography column to obtain 3,4-oxo-cyclo selenite galactose allyl glucoside. All of the above purification steps can adopt conventional operation methods in the art. In the present invention, the organic phase is preferably dried with anhydrous sodium sulfate, the dried organic phase is preferably evaporated to dryness on a rotary evaporator under reduced pressure, and the chromatographic column is preferably a silica gel column to obtain the pure 3,4-oxo-cyclo selenite galactose allyl glucoside. In the step of synthesizing 3,4-oxo-cyclo selenite galactose allyl glucoside in the present invention, the yield of which can reach more than 90%.

In the present invention, the acrylated polysaccharide is prepared by reacting acryloyl chloride with polysaccharides. The polysaccharides of the present invention are water-soluble natural polysaccharides containing 6-position primary hydroxyl groups, such as β-1-3-glucan, lentinan, schizophyllan, carrageenan of small molecular weight, and chitosan, and the like. Firstly, the polysaccharide is dissolved in a solvent. The solvent is not specifically limited in the present invention, and DMF can be used to dissolve polysaccharides. NaHCO₃, preferably solid sodium bicarbonate, is added to the polysaccharide solution. The molar ratio of the polysaccharide to sodium bicarbonate is preferably 1:5~50, more preferably 1.10~30. Acryloyl chloride is added dropwise to the polysaccharide solution, and the molar ratio of the polysaccharide to the dropped acryloyl chloride is preferably 1:1~50, more preferably 1:10~40, and still more preferably 1:20~30. During the dropwise addition, the temperature of the reaction solution is maintained to not exceed 40° C., more preferably 15~35'C It is preferred that the reaction is completed within 2~4 hours after the dropping is stopped. The reaction solution is poured into cold water, and cold ethanol is added to precipitate the acrylated polysaccharide. Preferably, the cold ethanol is added in an amount of 3~7 times the volume of the cold water of the reaction solution. The synthetic acrylated polysaccharide in the present invention is recovered at a rate of greater than 95%.

The acrylated polysaccharide of the present invention undergoes a displacement reaction with 3,4-oxo-cyclo selenite galactose allyl glucoside under the action of a Ru catalyst to obtain an esterified selenium polysaccharide. The Ru catalyst is not specifically limited in the present invention. In the specific embodiment of the present invention, the Grubbs-I generation Ru catalyst is preferred. The above-mentioned displacement reaction of the present invention is preferably performed in DMF solvent, preferably the acrylated polysaccharide is dissolved in DMF, 3,4-oxo-cyclo selenite galactose allyl glucoside is added, and finally a catalytic amount of Ru catalyst is added. In the present invention, it is preferred that the molar ratio of the acrylated polysaccharide to 3,4-oxo-cyclo selenite galactose allyl glycoside is 1:1~4, more preferably 1:2~3, preferably the Ru catalyst is added in an amount of 0.1~0.5 equivalent. In the present invention, it is preferred that the olefin replacement reaction, that is, bound of the organic selenium sugar unit on the polysaccharide, can be completed within 4~5 hours. The reaction solution is dispersed in the water phase, and the product is precipitated with 4~5 times the volume of ethanol at low temperature. Repeat of water-soluble-ethanol precipitation can purify the product with a yield of 80~95%.

The present invention also includes the esterified selenium polysaccharide prepared by the above preparation method, having a structural formula of:

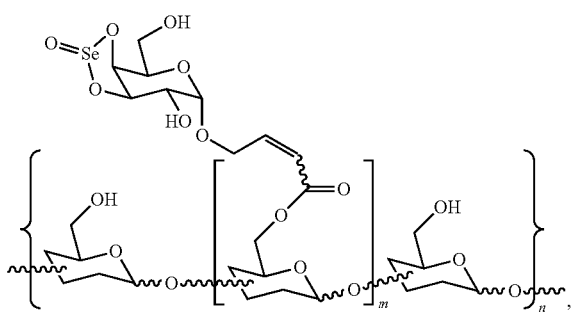

wherein M is the number of sugar units selenized, and N is the number of sugar units of natural polysaccharides. The organic selenium content of the esterified selenium polysaccharide prepared by the invention can reach 10,000 to 100,000 ppm.

The esterified selenium polysaccharide of the present invention has the potential to increase the selenium content in blood to improve many immune functions, and can be used in foods, medicines or health products to improve immune functions.

The specific embodiments described above further describe the purpose, technical solutions and beneficial effects of the present invention in further detail. It should be understood that the above descriptions are only specific embodiments of the present invention and are not intended to limit the protection scope of the present invention. Any modification, equivalent replacement, improvement, etc. made within the spirit and principle of the present invention shall be included in the protection scope of the present invention.

Examples of the present invention are provided below. The polysaccharide is exemplified by a commercially available water-soluble β-1-3-glucan, but it does not limit the protection scope of the present invention.

Example 1

1 equivalent of O=SeCl$_2$ was added dropwise to a commercially available D-galactose allyl glycoside DMSO solution containing 4 equivalents of triethylamine at 0° C. under the protection of nitrogen. The mixture was reacted at room temperature for 4 hours and poured into a water phase, extracted with ethyl acetate, and washed with saturated brine. The organic phase was dried with anhydrous sodium sulfate, evaporated to dryness under reduced pressure on a rotary evaporator, and purified by silica gel column chromatography to obtain a pure product with a yield greater than 90%.

100 mg of β-1-3-glucan was suspended in 10 ml of anhydrous DMF, 5 equivalents of solid sodium bicarbonate and 1 equivalent of acryloyl chloride were added while maintaining the temperature of the reaction solution to not exceed 40'C for a total of 2 hours. The reaction solution was poured into cold water with stirring, 4 times the volume of cold ethanol was added to precipitate the intermediate product, which was freeze-dried for later use. The above intermediate was resuspended in dry DMF, 1 equivalent of 3,4-oxo-cyclo selenite galactose allyl glucoside was added, and then 0.1 equivalent of Grubbs-1 generation Ru catalyst was added. The organic selenium polysaccharide was poured into the water phase after 4 hours and the product was precipitated with 4 times the volume of ethanol at low temperature ICP MS analyzed its selenium content to be 18,000 ppm.

Example 2

5 equivalents of O=SeCl$_2$ was added dropwise to a D-galactose allyl glycoside DMF solution containing 2 equivalents of triethylamine at 0° C. under the protection of nitrogen. The mixture was reacted at room temperature for 2 hours and poured into a water phase, extracted with ethyl acetate, and washed with saturated brine. The organic phase was dried with anhydrous sodium sulfate, evaporated to dryness under reduced pressure on a rotary evaporator, and purified by silica gel column chromatography to obtain a pure product with a yield greater than 90%.

100 mg of β-1-3-glucan was suspended in 20 ml of anhydrous DMF, 50 equivalents of solid sodium bicarbonate and 50 equivalents of acryloyl chloride were added while maintaining the temperature of the reaction solution to not exceed 40° C. for a total of 4 hours. The reaction solution was poured into cold water with stirring, 6 times the volume of cold ethanol was added to precipitate the intermediate product, which was freeze-dried for later use. The above intermediate was resuspended in dry DMF, 50 equivalents of 3,4-oxo-cyclo selenite galactose allyl glucoside was added, and then 0.5 equivalent of Grubbs-I generation Ru catalyst was added. The organic selenium polysaccharide was poured into the water phase after reaction for 5 hours and the product was precipitated with 5 times the volume of ethanol at low temperature. ICP MS analyzed its selenium content to be 96,000 ppm.

Example 3

3 equivalents of O=SeCl$_2$ was added dropwise to a D-galactose allyl glycoside DMF solution containing 3 equivalents of triethylamine at 0° C. under the protection of nitrogen. The mixture was reacted at room temperature for 3 hours and poured into a water phase, extracted with ethyl acetate, and washed with saturated brine. The organic phase was dried with anhydrous sodium sulfate, evaporated to dryness under reduced pressure on a rotary evaporator, and purified by silica gel column chromatography to obtain a pure product with a yield greater than 90%.

100 mg of β-1-3-glucan was suspended in 20 ml of anhydrous DMF, 20 equivalents of solid sodium bicarbonate and 20 equivalents of acryloyl chloride were added while maintaining the temperature of the reaction solution to not exceed 40° C. for a total of 4 hours. The reaction solution was poured into cold water with stirring, 5 times the volume of cold ethanol was added to precipitate the intermediate product, which was freeze-dried for later use. The above intermediate was resuspended in dry DMF, 20 equivalents of 3,4-oxo-cyclo selenite galactose allyl glucoside was added, and then 0.2 equivalent of Grubbs-I generation Ru catalyst was added. The organic selenium polysaccharide was poured into the water phase after reaction for 4 hours and the product was precipitated with 4 times the volume of ethanol at low temperature. ICP MS analyzed its selenium content to be 46,000 ppm.

Example 4

B-6 splenocytes were used as the experimental model. Carrageenan, chitohexaose, 1,3-glucose hexasaccharide, PMA+innomycin were used as controls and incubated in the culture medium containing the esterified selenium polysaccharide of the present invention (2 to 5 micrograms selenium/mL) for 48 hours to detect the expression of IL-4 and IFN-γ thereof.

In the Example, the culture medium for culturing B-6 spleen cells is the culture medium for culturing B-6 spleen cells conventionally in the art, and contains essential and non-essential amino acids, vitamins, glucose, hormones, growth factors, trace minerals and low-concentration fetal bovine serum (2%) and 5 mi penicillin/streptomycin solution. The buffer system of the medium is phosphate buffered saline solution PBS, and the pH value is 7.4 after equilibrating in a cell incubator containing 5% $CO_2$.

After the cells were harvested, they were stained with BD Bioscience's Cytofix/Cytoperm kit and detected by flow cytometry. The detection results were shown in FIGURE. 5. Compared with 1,3-glucose hexasaccharide, the maximum expression of IL-4 in B-6 splenocytes treated with the esterified selenium polysaccharide of the present invention can be significantly increased by 60%, and the maximum expression of IFN-γ is increased by 36%, indicating the use of the esterified selenium polysaccharide of the present invention can effectively improve the immunity of the system.

Example 5

Mice, which were used as a model, were fed with the esterified selenium polysaccharide prepared by the present invention continuously at a selenium dose of 2 to 5 micrograms of selenium/day for 2 weeks. A polysaccharide without the esterified selenium was used as a control. Blood detection was performed continuously from week 3 to week 6 (the esterified selenium was still fed during this period, the dosage was the same as before), once a week, and it was found that the selenium content in serum had increased by more than 30%, red blood cells increased by 20%, and white blood cells increased by 10%. The above-mentioned detection data became stable starting from week 5.

TABLE 1

Results of blood detection at different time periods after feeding mice

|  | Week 1 | | Week 3 | | Week 4 | | Week 5 | | Week 6 | |
| --- | --- | --- | --- | --- | --- | --- | --- | --- | --- | --- |
| Selenium supplement amount (μg/day) | 2 | 5 | 2 | 5 | 2 | 5 | 2 | 5 | 2 | 5 |
| Selenium content in serum (μg/L) | 0.4 | 0.7 | 2.9 | 4.5 | 6.1 | 6.8 | 6.9 | 7.3 | 7.0 | 7.3 |
| red blood cell (×10$^6$/mL) | 9.58 | 9.66 | 9.75 | 9.97 | 10.5 | 10.5 | 11.1 | 11.4 | 11.2 | 11.5 |
| white blood cell (×10$^3$/mL) | 7.26 | 7.29 | 7.36 | 7.57 | 7.59 | 7.91 | 7.96 | 7.99 | 7.96 | 7.99 |

Example 6

Chicks, which were used as a model, were fed with the esterified selenium polysaccharide of the present invention continuously at a dose of 5 micrograms of selenium/day after birth. A polysaccharide without the esterified selenium was used as a control. On days 7, 14, 21, and 28 after feeding, the assay of the activity of glutathione peroxidase (GSH-Px) and superoxide dismutase (SOD) was performed (using commercially available kits EnzyChrom™ Glutahione Peroxidase Assay Kit and MIBio Mouse superoxide dismutase (SOD) kit for completion of the assay). The results showed that the chick GHS-Px activity reached the maximum on days 14-21 with an increase by 15%, and the SOD reached the maximum on days 7-14 with an increase by 12%, indicating that the esterified selenium polysaccharide of the present invention has better antioxidant function.

TABLE 2

Activities of GSH-Px and SOD in different time periods of feeding chicks

| (U/mg) | Day 1 | Day 7 | Day 14 | Day 21 | Day 28 |
| --- | --- | --- | --- | --- | --- |
| Serum GSH-Px | 1869 | 1879 | 1975 | 2150 | 2090 |
| Serum SOD | 180 | 191 | 195 | 190 | 187 |

The specific embodiments described above further describe the purpose, technical solutions and beneficial effects of the present invention in further detail. It should be understood that the above descriptions are merely specific embodiments of the present invention and are not intended to limit the protection scope of the present invention. Any modification, equivalent replacement, improvement, etc. made within the spirit and principle of the present invention shall be included in the protection scope of the present invention.

What is claimed is:

1. A method for preparing an esterified selenium polysaccharide, comprising the following steps:
   1) adding 1-5 equivalents of O=$SeCl_2$ dropwise to a D-galactose allyl glucoside solution containing 1-5 equivalents of triethylamine at 0° C. under a protection of nitrogen, reacting at room temperature for 1-4 hours to obtain a first reaction solution, then pouring the first reaction solution into a first water phase to obtain a mixture, and extracting the mixture with ethyl acetate to obtain 3,4-oxo-cyclo selenite galactose allyl glucoside;
   2) suspending a polysaccharide in a first solvent, mixing with a sodium bicarbonate ($NaHCO_3$) to obtain a polysaccharide solution, adding acryloyl chloride dropwise to the polysaccharide solution to obtain a second reaction solution, and maintaining a temperature of the second reaction solution to not exceed 40° C. during a dropwise addition, after completion of a reaction of the second reaction solution, dissolving the second reaction solution in water and performing an alcohol precipitation to obtain acrylated polysaccharide; and
   3) dissolving the acrylated polysaccharide in a second solvent, performing a displacement reaction of the acrylated polysaccharide with the 3,4-oxo-cyclo selenite galactose allyl glucoside under an action of a Ru catalyst to obtain a third reaction solution, dispersing the third reaction solution in a second water phase and performing the alcohol precipitation to obtain the esterified selenium polysaccharide;
   wherein step 1) and step 2) are not limited in order.

2. The method according to claim 1, wherein in step 2), a molar ratio of the polysaccharide to the sodium bicarbonate is 1:5-50.

3. The method according to claim 1, wherein in step 2), the reaction of the second reaction solution is completed 2-3 hours after the dropwise addition is stopped.

4. The method according to claim 1, wherein in step 3), a molar ratio of the acrylated polysaccharide to the 3,4-oxo-cyclo selenite galactose allyl glucoside is 1: 1-4.

5. The method according to claim 1, wherein in step 3), the displacement reaction is completed within 4-5 hours.

6. The method according to claim 1, wherein step 1) further comprises a purification step after extracting the mixture with the ethyl acetate, wherein the purification step comprises:
washing an extract with a saturated brine, drying an organic phase and evaporating the organic phase to dryness, and loading the organic phase on a chromatography column to obtain the 3,4-oxo-cyclo selenite galactose allyl glucoside.

7. The method according to claim 1, wherein the polysaccharide is a water-soluble natural polysaccharide containing a primary hydroxyl group at a 6-position.

8. An esterified selenium polysaccharide prepared by the method according to claim 1, wherein the esterified selenium polysaccharide comprises a structural formula of:

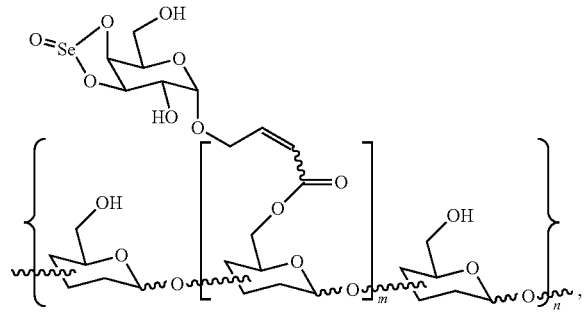

wherein in is a number of sugar units selenized, and n is a number of sugar units of natural polysaccharides.

9. The esterified selenium polysaccharide according to claim 8, wherein an organic selenium content of the esterified selenium polysaccharide reaches 10,000 to 100,000 ppm.

10. The method according to claim 2, wherein in step 2), the reaction of the second reaction solution is completed 2-3 hours after the dropwise addition is stopped.

11. The esterified selenium polysaccharide according to claim 8, wherein in step 2), a molar ratio of the polysaccharide to the sodium bicarbonate is 1:5-50.

12. The esterified selenium polysaccharide according to claim 8, wherein in step 2), the reaction of the second reaction solution is completed 2-3 hours after the dropwise addition is stopped.

13. The esterified selenium polysaccharide according to claim 8, wherein in step 3), a molar ratio of the acrylated polysaccharide to the 3,4-oxo-cyclo selenite galactose allyl glucoside is 1: 1-4.

14. The esterified selenium polysaccharide according to claim 8, wherein in step 3), the displacement reaction is completed within 4-5 hours.

15. The esterified selenium polysaccharide according to claim 8, wherein step 1) further comprises a purification step after extracting the mixture with the ethyl acetate, wherein the purification step comprises:
washing an extract with a saturated brine, drying an organic phase and evaporating the organic phase to dryness, and loading the organic phase on a chromatography column to obtain the 3,4-oxo-cyclo selenite galactose allyl glucoside.

16. The esterified selenium polysaccharide according to claim 8, wherein the polysaccharide is a water-soluble natural polysaccharide containing a primary hydroxyl group at a 6-position.

* * * * *